(12) United States Patent
Gellissen et al.

(10) Patent No.: US 7,858,343 B2
(45) Date of Patent: Dec. 28, 2010

(54) METHOD FOR PRODUCTION OF A HETEROLOGOUS PROTEIN USING YEAST-TYPE HOST CELLS

(75) Inventors: Gerd Gellissen, Wülfrath (DE); Jens Klabunde, Düsseldorf (DE); Cornelis Hollenberg, Düsseldorf (DE); Adelheid Degelmann, Düsseldorf (DE)

(73) Assignee: Artes Biotechnology GmbH, Essen (DE)

( * ) Notice: Subject to any disclaimer, the term of this patent is extended or adjusted under 35 U.S.C. 154(b) by 774 days.

(21) Appl. No.: 11/667,935

(22) PCT Filed: Nov. 8, 2005

(86) PCT No.: PCT/EP2005/011942

§ 371 (c)(1),
(2), (4) Date: May 16, 2007

(87) PCT Pub. No.: WO2006/053656

PCT Pub. Date: May 26, 2006

(65) Prior Publication Data

US 2008/0118950 A1    May 22, 2008

(30) Foreign Application Priority Data

Nov. 17, 2004 (EP) .................. 04027280

(51) Int. Cl.
*C12P 21/06* (2006.01)
(52) U.S. Cl. .................................. 435/69.1
(58) Field of Classification Search ................ 435/69.1
See application file for complete search history.

(56) References Cited

PUBLICATIONS

Klabunde: "Koproduktion Pharmazeutischer Proteine and Hilfsfaktoren zur Optimierung mikrobieller Expressionssysteme bei Beschrankung auf ein einziges integratives Vektorsystem", 2003, Universitats- Und Landesbibliothek Dusseldorf, Dusseldorf, Deutschland.

Punt P. J et al: "Filamentous Fungi as cell factories for heterologous protein production", Trends in Biotechnology, Elsevier Publications, Cambridge, GB, Bd. 20, Nr. 5, May 1, 2002, pp. 200-206.
De Virgilio Claudio et al: "CNE1, a *Saccharomyces cerevisiae* homologue of the genes encoding mammalian calnexin and calreticulin", Yeast, Bd. 9, Nr. 2, 1993, pp. 185-188.
Higgins M K et al: "Calnexin co-expression and the use of weaker promoters increase the expression of correctly assembled Shaker potassium channel in insect cells", Biochimica Et Biophysica Acta. Biomembranes, Amsterdam, NL, Bd. 1610, Nr. 1, Feb. 17, 2003, pp. 124-132.
Marechal Alexandre et al: "Cell viability and secretion of active proteins in *Schizosaccharomyces pombe* do not require the chaperone function of calnexin", The Biochemical Journal, Jun. 1, 2004, Bd. 380, Nr. Pt 2, Jun. 1, 2004, pp. 441-448.
Arima et al: "Enhanced secretion of hydrophobic peptide fused lysozyme by the introduction of N-glycosylation signal and the disruption of calnexin gene in *Saccharomyces cerevisiae*", FEBS Letters 440 (1998), pp. 89-92.
Klabunde et al: "Integration of heterologous genes in several yeast species using -vectors containing a *Hansenula polymorpha*-derived rDNA-targeting element", FEMS Yeast Research 4 (2003), pp. 185-193.
Gellissen, G. (ed), "*Hansenula polymorpha*—biology and applications", Wiley-VCH, Weinheim 2002, Chapter 8, Suckow et al., "The expression platform based on *H. polymorpha* strain RB11 and its derivatives—history, status and perspectives" pp. 105-123; and Chapter 17, Degelmann, "Methods" pp. 285-335.

*Primary Examiner*—Maryam Monshipouri
(74) *Attorney, Agent, or Firm*—Fay Sharpe LLP (57) ABSTRACT

A heterologous protein is produced by a method in which yeast-type host cells are prepared, which, in addition to the at least one endogenous homologous DNA sequence coding for a first calnexin, includes at least one recombinant DNA sequence coding for the protein and at least one additional recombinant DNA sequence coding for at least one second calnexin. The protein in the host cell represents a heterologous secretable protein. The host cells are induced to express the heterologous protein via the at least one sequence coding for the protein and to overexpress calnexins by the at least one additional sequence coding for the at least one second calnexin. The host cells are then induced to secrete the heterologous protein. The secreted heterologous protein is then separated off.

22 Claims, 4 Drawing Sheets

Calnexin H. polymorpha (CNE1)
NH₂-
MKVSRPIILLFLSLVSYAADVERKDFLPLSLESDAFFEQFNETWASRWKPSHSKRDENFV
YRGEWDVEEPTVNPGLKGDKGLVAKTEAAHHAISARLPTPFDNTNNTLVLQYEVKLQKGL
ECGGAYIKLLSQEGGVSDSVEFSNDTPYQVMFGPDKCGMSNKVHFILRRKNPKTGEYEEK
HLKVPPMARIVKTSTLYTLIIKPNQDFEIRINGEVAKAGSLLDSRYFDLTPPKEIDDPND
EKPADWVDDELIPDPNAVKPEDWDEDAPYLIPDPNAVKPEDWDEDAEAYIPDPDAVKPEY
WDEEEDGEWIAPKIPNPACEQHGCGPWSAPKIRNPDYKGKWTPELIENPDYKGPWSPRKI
PNPEYYEDPTPSNLEPIGALGFELWTNTDSIMFDNIYLGHSIEEAEYIGNNTFLPKVEIE
EQIAAANAPQAKYDAEEPEKQIEEQSLVSDLLDKSVDRVLKVYASGKAYWADLLDDPTKT
LLNRPGEAFFFASVVVGTITTTFAISTTIVSIFATLFAPSTPQPVKRSEAKERIESVKEK
ATASDSKVNETEAVKRG
- COO²⁻

Figure 1A

Calnexin S. cerevisiae (CNE1)
NH₂ -
MKFSAYLWWLFLNLALVKGTSLLSNVTLAEDSFWEHFQAYTNTKHLNQEWITSEAVNNEG
SKIYGAQWRLSQGRLQGSAWDKGIAVRTGNAAAMIGHLLETPINVSETDTLVVQYEIKLD
NSLTCGGAFIKLMSGFMNVEALKHYAPDTEGVELVFGPDYCAPEINGVQFAINKVDKITH
ESKLRYLQEMPLSKLTDTSQSHLYTLIIDESAQSFQILIDGKTVMVREHIEDKKKVNFEP
PITPPLMIPDVSVAKPHDWDDRIRIPDPEAVKLSDRDERDPLMIPHPDGTEPPEWNSSIP
EYILDPNAQKPSWWKELEHGEWIPPMIKNPLCTAERGCGQQIPGLINNAKYKGPGELNEI
INPNYMGEWHPPEIENPLYYEEQHPLRIENVISGVILEFWSGSPNMLISNIYVGKNVTEA
QIIGNKTWLMRDRAFRGSDGPTERKFMNSRLGNLQTTFHNERESPNPFDRIIDRILEQPL
KFVLTAAVVLLTTSVLCCVVFT
- COO²⁻

Figure 1B

```
11 Nov 2004              Molecule Information

Molecule:      HCNE-Phleo(d), 8102 bps DNA Circular
File Name:     HCNE-Phleo(d).cm5, dated 11 Nov 2004

Molecule Features:

Type      Start    End     Name       Description

GENE         69     13  C             MOX-T.
MARKER      258                       T -> C  (creates StuI site)
MARKER     1799                       A -> G; stiller Basenaustausch (Glu-
>Glu)
GENE       1969    296  C  HCNE
REGION     2390     84  C
GENE       2882   2413  C  HARS1      HARS1
REGION     3539   3039  C             URA3 gene from S. cerevisiae +D4
GENE       3824   3548  C             CYC1-T (S. cerevisiae)
GENE       4290   3910  C  Tn5 ble    Tn5 ble
GENE       4722   4305  C             TEF1-P (S. cerevisiae)
REGION     5185   4732  C             URA3 gene from S. cerevisiae +D4
REGION     6219   6886     ori
GENE       7891   7031  C  ampR       ß-lactamase
```

Figure 2

| 11 Nov 2004 | | | Molecule Information | |
|---|---|---|---|---|

Molecule: TEFP-HCNE-Phleo(d), 8036 bps DNA Circular
File Name: TEFP-HCNE-Phleo(d).cm5, dated 11 Nov 2004

Molecule Features:

| Type | Start | End | Name | Description |
|---|---|---|---|---|
| GENE | 69 | 13 C | | MOX-T. |
| MARKER | 258 | | | T -> C (creates StuI site) |
| REGION | 1969 | 84 C | | |
| GENE | 1969 | 296 C | HCNE | |
| REGION | 2303 | 2007 C | TEF1-P | TEF1-Promotor aus A.adeninivorans |
| GENE | 2816 | 2347 C | HARS1 | HARS1 |
| REGION | 3473 | 2973 C | | URA3 gene from S. cerevisiae +D4 |
| GENE | 3758 | 3482 C | | CYC1-T (S. cerevisiae) |
| GENE | 4224 | 3844 C | Tn5 ble | Tn5 ble |
| GENE | 4656 | 4239 C | | TEF1-P (S. cerevisiae) |
| REGION | 5119 | 4666 C | | URA3 gene from S. cerevisiae +D4 |
| REGION | 6153 | 6820 | ori | |
| GENE | 7825 | 6965 C | ampR | ß-lactamase |

SEQUENCE LISTING

<160> NUMBER OF SEQ ID NOS: 2

<210> SEQ ID NO 1
<211> LENGTH: 557
<212> TYPE: PRT
<213> ORGANISM: Hansenula polymorpha

<400> SEQUENCE: 1

```
Met Lys Val Ser Arg Pro Ile Ile Leu Leu Phe Leu Ser Leu Val Ser
1               5                   10                  15

Tyr Ala Ala Asp Val Glu Arg Lys Asp Phe Leu Pro Leu Ser Leu Glu
            20                  25                  30

Ser Asp Ala Phe Phe Glu Gln Phe Asn Glu Thr Trp Ala Ser Arg Trp
        35                  40                  45

Lys Pro Ser His Ser Lys Arg Asp Glu Asn Phe Val Tyr Arg Gly Glu
    50                  55                  60

Trp Asp Val Glu Glu Pro Thr Val Asn Pro Gly Leu Lys Gly Asp Lys
65                  70                  75                  80

Gly Leu Val Ala Lys Thr Glu Ala Ala His His Ala Ile Ser Ala Arg
                85                  90                  95

Leu Pro Thr Pro Phe Asp Asn Thr Asn Asn Thr Leu Val Leu Gln Tyr
            100                 105                 110

Glu Val Lys Leu Gln Lys Gly Leu Glu Cys Gly Gly Ala Tyr Ile Lys
        115                 120                 125

Leu Leu Ser Gln Glu Gly Gly Val Ser Asp Ser Val Glu Phe Ser Asn
    130                 135                 140

Asp Thr Pro Tyr Gln Val Met Phe Gly Pro Asp Lys Cys Gly Met Ser
145                 150                 155                 160

Asn Lys Val His Phe Ile Leu Arg Arg Lys Asn Pro Lys Thr Gly Glu
                165                 170                 175

Tyr Glu Glu Lys His Leu Lys Val Pro Pro Met Ala Arg Ile Val Lys
            180                 185                 190

Thr Ser Thr Leu Tyr Thr Leu Ile Ile Lys Pro Asn Gln Asp Phe Glu
        195                 200                 205

Ile Arg Ile Asn Gly Glu Val Ala Lys Ala Gly Ser Leu Leu Asp Ser
    210                 215                 220

Arg Tyr Phe Asp Leu Thr Pro Pro Lys Glu Ile Asp Pro Asn Asp
225                 230                 235                 240

Glu Lys Pro Ala Asp Trp Val Asp Glu Leu Ile Pro Asp Pro Asn
                245                 250                 255

Ala Val Lys Pro Glu Asp Trp Asp Glu Asp Ala Pro Tyr Leu Ile Pro
            260                 265                 270

Asp Pro Asn Ala Val Lys Pro Glu Asp Trp Asp Glu Asp Ala Glu Ala
        275                 280                 285

Tyr Ile Pro Asp Pro Asp Ala Val Lys Pro Glu Tyr Trp Asp Glu Glu
    290                 295                 300

Glu Asp Gly Glu Trp Ile Ala Pro Lys Ile Pro Asn Pro Ala Cys Glu
305                 310                 315                 320

Gln His Gly Cys Gly Pro Trp Ser Ala Pro Lys Ile Arg Asn Pro Asp
                325                 330                 335

Tyr Lys Gly Lys Trp Thr Pro Glu Leu Ile Glu Asn Pro Asp Tyr Lys
            340                 345                 350

Gly Pro Trp Ser Pro Arg Lys Ile Pro Asn Pro Glu Tyr Tyr Glu Asp
```

-continued

```
                355                 360                 365
Pro Thr Pro Ser Asn Leu Glu Pro Ile Gly Ala Leu Gly Phe Glu Leu
    370                 375                 380

Trp Thr Met Thr Asp Ser Ile Met Phe Asp Asn Ile Tyr Leu Gly His
385                 390                 395                 400

Ser Ile Glu Glu Ala Glu Tyr Ile Gly Asn Asn Thr Phe Leu Pro Lys
                405                 410                 415

Val Glu Ile Glu Glu Gln Ile Ala Ala Asn Ala Pro Gln Ala Lys
                420                 425                 430

Tyr Asp Ala Glu Glu Pro Glu Lys Gln Ile Glu Glu Gln Ser Leu Val
            435                 440                 445

Ser Asp Leu Leu Asp Lys Ser Val Asp Arg Val Leu Lys Val Tyr Ala
    450                 455                 460

Ser Gly Lys Ala Tyr Trp Ala Asp Leu Leu Asp Asp Pro Thr Lys Thr
465                 470                 475                 480

Leu Leu Asn Arg Pro Gly Glu Ala Phe Phe Phe Ala Ser Val Val Val
                485                 490                 495

Gly Thr Ile Thr Thr Thr Phe Ala Ile Ser Thr Thr Ile Val Ser Ile
                500                 505                 510

Phe Ala Thr Leu Phe Ala Pro Ser Thr Pro Gln Pro Val Lys Arg Ser
            515                 520                 525

Glu Ala Lys Glu Arg Ile Glu Ser Val Lys Glu Lys Ala Thr Ala Ser
    530                 535                 540

Asp Ser Lys Val Asn Glu Thr Glu Ala Val Lys Arg Gly
545                 550                 555

<210> SEQ ID NO 2
<211> LENGTH: 502
<212> TYPE: PRT
<213> ORGANISM: Saccharomyces cerevisiae

<400> SEQUENCE: 2

Met Lys Phe Ser Ala Tyr Leu Trp Trp Leu Phe Leu Asn Leu Ala Leu
1               5                   10                  15

Val Lys Gly Thr Ser Leu Leu Ser Asn Val Thr Leu Ala Glu Asp Ser
                20                  25                  30

Phe Trp Glu His Phe Gln Ala Tyr Thr Asn Thr Lys His Leu Asn Gln
            35                  40                  45

Glu Trp Ile Thr Ser Glu Ala Val Asn Asn Glu Gly Ser Lys Ile Tyr
    50                  55                  60

Gly Ala Gln Trp Arg Leu Ser Gln Gly Arg Leu Gln Gly Ser Ala Trp
65                  70                  75                  80

Asp Lys Gly Ile Ala Val Arg Thr Gly Asn Ala Ala Ala Met Ile Gly
                85                  90                  95

His Leu Leu Glu Thr Pro Ile Asn Val Ser Thr Asp Thr Leu Val
            100                 105                 110

Val Gln Tyr Glu Ile Lys Leu Asp Asn Ser Leu Thr Cys Gly Gly Ala
    115                 120                 125

Phe Ile Lys Leu Met Ser Gly Phe Met Asn Val Glu Ala Leu Lys His
130                 135                 140

Tyr Ala Pro Asp Thr Glu Gly Val Glu Leu Val Phe Gly Pro Asp Tyr
145                 150                 155                 160

Cys Ala Pro Glu Ile Asn Gly Val Gln Phe Ala Ile Asn Lys Val Asp
                165                 170                 175
```

-continued

```
Lys Ile Thr His Glu Ser Lys Leu Arg Tyr Leu Gln Glu Met Pro Leu
            180                 185                 190

Ser Lys Leu Thr Asp Thr Ser Gln Ser His Leu Tyr Thr Leu Ile Ile
        195                 200                 205

Asp Glu Ser Ala Gln Ser Phe Gln Ile Leu Ile Asp Gly Lys Thr Val
    210                 215                 220

Met Val Arg Glu His Ile Glu Asp Lys Lys Val Asn Phe Glu Pro
225                 230                 235                 240

Pro Ile Thr Pro Pro Leu Met Ile Pro Asp Val Ser Val Ala Lys Pro
                245                 250                 255

His Asp Trp Asp Asp Arg Ile Arg Ile Pro Asp Pro Glu Ala Val Lys
            260                 265                 270

Leu Ser Asp Arg Asp Glu Arg Asp Pro Leu Met Ile Pro His Pro Asp
        275                 280                 285

Gly Thr Glu Pro Pro Glu Trp Asn Ser Ser Ile Pro Glu Tyr Ile Leu
    290                 295                 300

Asp Pro Asn Ala Gln Lys Pro Ser Trp Trp Lys Glu Leu Glu His Gly
305                 310                 315                 320

Glu Trp Ile Pro Pro Met Ile Lys Asn Pro Leu Cys Thr Ala Glu Arg
                325                 330                 335

Gly Cys Gly Gln Gln Ile Pro Gly Leu Ile Asn Asn Ala Lys Tyr Lys
            340                 345                 350

Gly Pro Gly Glu Leu Asn Glu Ile Ile Asn Pro Asn Tyr Met Gly Glu
        355                 360                 365

Trp His Pro Pro Glu Ile Glu Asn Pro Leu Tyr Tyr Glu Glu Gln His
    370                 375                 380

Pro Leu Arg Ile Glu Asn Val Ile Ser Gly Val Ile Leu Glu Phe Trp
385                 390                 395                 400

Ser Gly Ser Pro Asn Met Leu Ile Ser Asn Ile Tyr Val Gly Lys Asn
                405                 410                 415

Val Thr Glu Ala Gln Ile Ile Gly Asn Lys Thr Trp Leu Met Arg Asp
            420                 425                 430

Arg Ala Phe Arg Gly Ser Asp Gly Pro Thr Glu Arg Lys Phe Met Asn
        435                 440                 445

Ser Arg Leu Gly Asn Leu Gln Thr Thr Phe His Asn Glu Arg Glu Ser
    450                 455                 460

Pro Asn Pro Phe Asp Arg Ile Ile Asp Arg Ile Leu Glu Gln Pro Leu
465                 470                 475                 480

Lys Phe Val Leu Thr Ala Ala Val Val Leu Leu Thr Thr Ser Val Leu
                485                 490                 495

Cys Cys Val Val Phe Thr
            500
```

METHOD FOR PRODUCTION OF A HETEROLOGOUS PROTEIN USING YEAST-TYPE HOST CELLS

This application is a 371 of PCT/EP05/11942, filed Nov. 8, 2005, which claims foreign priority to European Patent Application 04027280.9 filed Nov. 17, 2004.

BACKGROUND

The invention relates to a method for production of a heterologous protein, for which host cells of a yeast type are prepared that contain in each case at least one recombinant DNA sequence coding for the heterologous protein, then the host cells are caused to express and secrete the heterologous protein, and the secreted, heterologous protein is separated.

Methods of the type mentioned in the introduction are known, for example, from publication WO 00/68400 A1. The obtaining of proteins, which, for example, are used as active compounds in medications, with the help of recombinant DNA technology, has, among others, the advantage that the proteins can be made available in well characterised hosts in practically unlimited quantities. It is advantageous for the obtaining of recombinant proteins if, in each case, the expressed protein is secreted so that it can subsequently be obtained from the cell supernatant. This greatly simplifies the preparation, because the protein is already available in a relatively pure form and costly purification steps can be avoided. In many cases, yeasts are used in order to obtain secreted proteins on a large scale. These have the advantage that they can be kept relatively simply in cell cultures and lead to a good yield.

It is always the aim to increase the secretion of the heterologous proteins. In order to achieve this, it was proposed, for example, to increase the number of copies of the recombinant DNA sequences that code for the heterologous protein. Further, for an increase in yield of the protein, usually secreted in glycosylated form, it was proposed by Arima et al in 'Enhanced secretion of hydrophobic peptide fused lysozyme by the introduction of N-glycosylation signal and the disruption of calnexin gene in *Saccharomyces cerevisiae*,' *PEBS Letters* 440 (1998), pages 89-92, to deactivate the gene of the yeast cells that code for the chaperone calnexin. Based on the results of this work, it can be expected that the calnexin reduces the secretion of heterologous proteins from yeast cells. In 'Calnexin Overexpression Increases Manganese Peroxidase Production in *Asperigillus niger*,' in *Applied and Environment Microbiology*, February 2002, pages 846-851, Conesa et al describe that an overexpression of calnexin increases the production of manganese peroxidase; however, on the one hand, this applied to filamentous fungus cultures, and, on the other hand, the positive influence of the calnexin overexpression on the yield was caused by the calnexin influencing heme incorporation into the manganese peroxidase.

BRIEF SUMMARY

The task of the invention is to provide a method by which the secretion of a heterologous protein is increased using yeast host cells. The task is solved by a method with the features of claim 1.

Using the method according to the invention for production of a protein, host cells were initially provided from at least the yeast strains of the genera *Saccharomyces, Schizosaccharomyces, Kluyveromyces, Hansenula, Pichia, Arxula, Schwanniomyces, Candida*, or *Yarrowia*, which, along with their at least one own homologous DNA sequence coding for at least a first calnexin, they also contained in each case at least one recombinant DNA sequence coding for the protein, as well as at least one additional recombinant DNA sequence coding for a second calnexin, whereby the protein in the host cell represents a heterologous secretable protein. For example, the host cell contains a homologous DNA sequence, which codes for a first (own) calnexin. However, the host cells can also contain several of their own homologous DNA sequences, which code for a calnexin or also several different calnexins. According to the invention, the host cells to be prepared contain one or more additional recombinant DNA sequences, which code for at least a second calnexin. The terms 'first' and 'second' calnexin are used in the scope of this invention description to distinguish the homologous DNA sequence coded calnexin already present, on one hand, from the additional heterologous DNA sequence coded calnexins. However, the use of these terms alone does not imply a structural difference. The additional recombinant DNA sequences can comprise several different recombinant DNA sequences that code for the same or different (second) calnexins. Preferably, however, they are several copies of the same recombinant DNA sequence, which all code for the same second calnexin. Preferably, the second calnexin (the recombinant DNA sequence coding for that) is structurally similar or the same ('structurally similar' will be used here to mean that, on the one hand, codons that code for the same amino acid can be exchanged for one another, and, furthermore, that individual codons can be exchanged for codons that code for other amino acids, to the extent that the functions of the calnexin are thereby influenced at most insignificantly) as the first calnexin (coding for its own, homologous DNA sequence). A calnexin, in general, is a chaperone in the endoplasmic reticulum (ER) in any cell of an organism that, through binding on the oligosaccharide Glc1Man9-GlcNAc2, is involved in the folding and quality control of newly originating glycoproteins until these proteins are correctly folded or—because of an incorrect folding—are led to degradation. The term 'a calnexin' should—unless otherwise stated—include a calnexin from a yeast cell (CNE) as well as a calnexin (CNX) or calreticulin (CNR) from a mammalian cell or corresponding proteins from another cell.

The host cells are caused, with the help of at least one sequence coding for the protein, to express the heterologous protein, and with the help of at least one additional sequence coding for at least a second calnexin, to overexpress calnexins. Subsequently, the host cells are caused to secrete the heterologous protein. Finally, the secreted heterologous protein is separated.

In view of the state of the art described previously, the increasing effect of the overexpression of calnexins on the secretion of heterologous proteins in yeast cells is surprising. It is also surprising that a further increase of the protein secretion through calnexin overexpression has even been detected when the host cells already show a high yield of the secreted heterologous protein, even without calnexin overexpression.

In the preferred embodiment of the method according to the invention, during the host cell preparation step, at least one sequence coding for the heterologous protein and at least one additional DNA sequence coding for at least a second calnexin are inserted into the host cells with the help of vectors. Here, the vectors can be present in the cells as free plasmids. However, it is preferable for the particular vectors to be integrated into the genome of the cell.

The recombinant DNA sequences coding for the heterologous protein, on the one hand, and the additional recombinant DNA sequence coding for at least one second calnexin, on the other, can be present on the same vector. Preferably, however, every DNA sequence coded for the heterologous protein and every DNA sequence coding for a second calnexin is inserted on a corresponding separate vector. This simplifies the preparation of the vectors.

The host cells can be prepared in different ways. For example, recombinant host cells can be prepared initially that contain at least one recombinant DNA sequence coding for the heterologous protein, and the recombinant host cells can subsequently be supertransformed, in which in each case at least one additional DNA sequence coding for a second calnexin is inserted into the recombinant host cells with the aid of vectors. Alternatively, the host cells could be prepared, whereby the recombinant host cells are first prepared that contain in each case at least one additional DNA sequence coding for at least a second calnexin, and the recombinant host cells can subsequently be supertransformed by insertion of in each case at least one recombinant DNA sequence coding for the heterologous protein in the recombinant host cells. Finally, it is also conceivable that during the step of preparing the host cells step at least one recombinant DNA sequence for the heterologous protein as well as at least one recombinant DNA sequence coding for at least a second calnexin are inserted into the host cell at the same time. For all three variants mentioned, appropriate expression plasmids are prepared as vectors before the step of preparing the host cells, whereby the vector in each case contains a DNA sequence coding for at least a second calnexin or a DNA sequence coding for the heterologous protein. The last-mentioned expression plasmids are prepared by isolating a calnexin gene (for example from the yeast type of host cells), and cloning it into a plasmid, whereby the calnexin gene is inserted between a homologous or a heterologous promoter and a homologous or heterologous terminator.

In a preferred embodiment of the method according to the invention, in step a) the host cells of a methylotrophic yeast are prepared, in particular a yeast of the genera *Hansenula* and *Picia*. Particularly preferable are host cells of the yeast *Hansenula polymorpha*.

In a preferred embodiment, the host cells of a recombinant yeast are prepared that contain in each case at least one recombinant DNA sequence coding for a heterologous protein, where the heterologous protein is a protein that during the expression and/or secretion is post-translationally modified, in particular post-translationally glycosylated. In doing so, the protein is a protein from a group that includes, for example, γ-interferon, alginate epimerase, and consensus phytase.

In another embodiment, the heterologous protein is preferably a protein from a group that contains γ-interferon, α-interferon, hirudin, serum albumins, alginate epimerase and consensus phytase.

Advantageous and/or preferable further developments of the method according to the invention are characterised in the dependent claims.

In the following, the invention is described in more detail using preferred embodiments. In the drawings.

BRIEF DESCRIPTION OF THE DRAWINGS

DETAILED DESCRIPTION

Initially, host cells of a yeast type are prepared that contain, along with their own homologous DNA sequence coding for calnexin, several copies of a recombinant DNA sequence coded for a heterologous protein, as well as several copies of an additional recombinant DNA sequence coding for calnexin. Preferably, recombinant *Hansenula polymorpha* host cells are prepared.

Figure 1A:
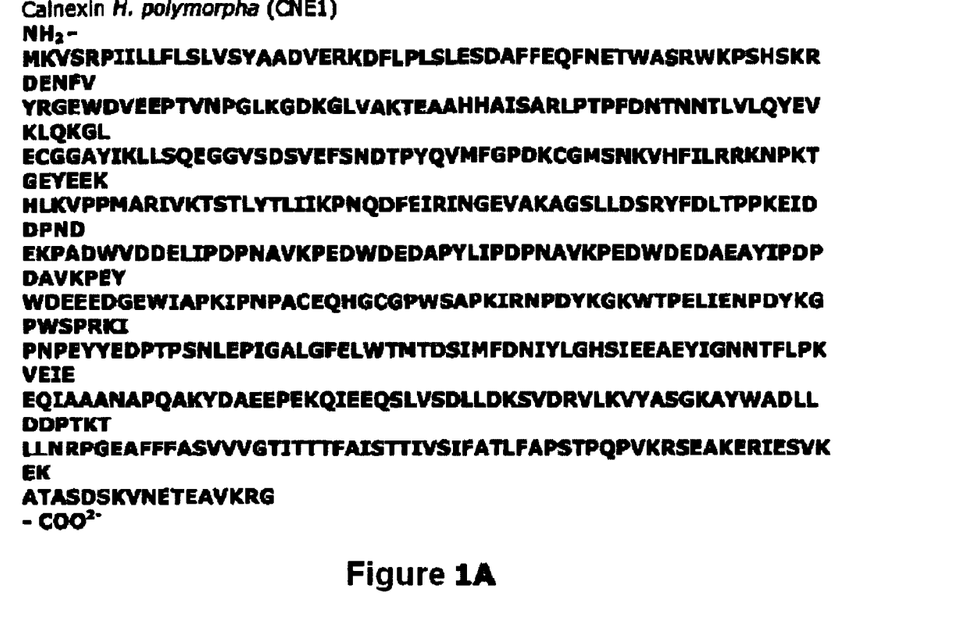
FIG. 1A and 1B show the DNA sequences coding for the additional calnexin for insertion into the host cells (the appendixes 2A and 2B show the associated sequence listing)
Figure 1B:
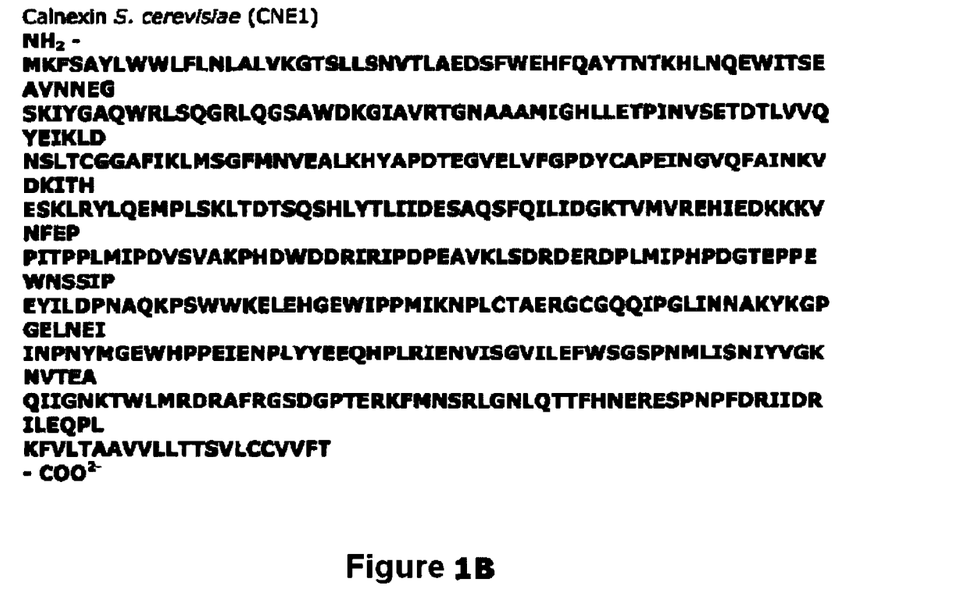

To producer the recombinant host cells, expression plasmids are first prepared as vectors. For this, the calnexin gene of the yeast *Hansenula polymorpha*, shown in FIG. 1A and appendix 2A (the homologue of the calnexin gene CNE1 of *Saccharomyces cerevisiae*—cf FIG. 1B), from a *Hansenula polymorpha* strain with the name RB11 was isolated, cloned, and sequenced using a polymerase chain reaction.

Figure 2:
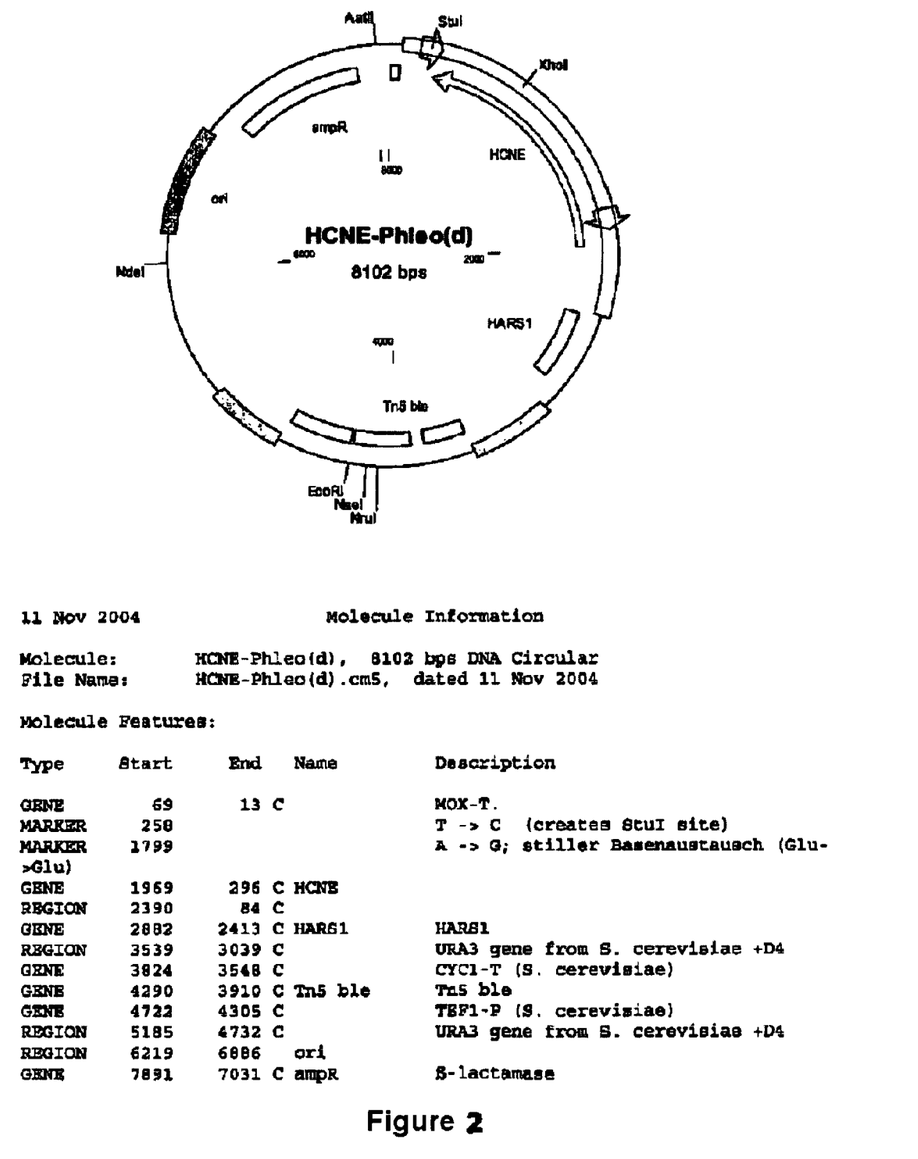
FIG. 2 shows a plasmid type of a calnexin expression plasmid, HCNE-Phleo, used for the supertransformation of a recombinant yeast host cell.
Figure 3:
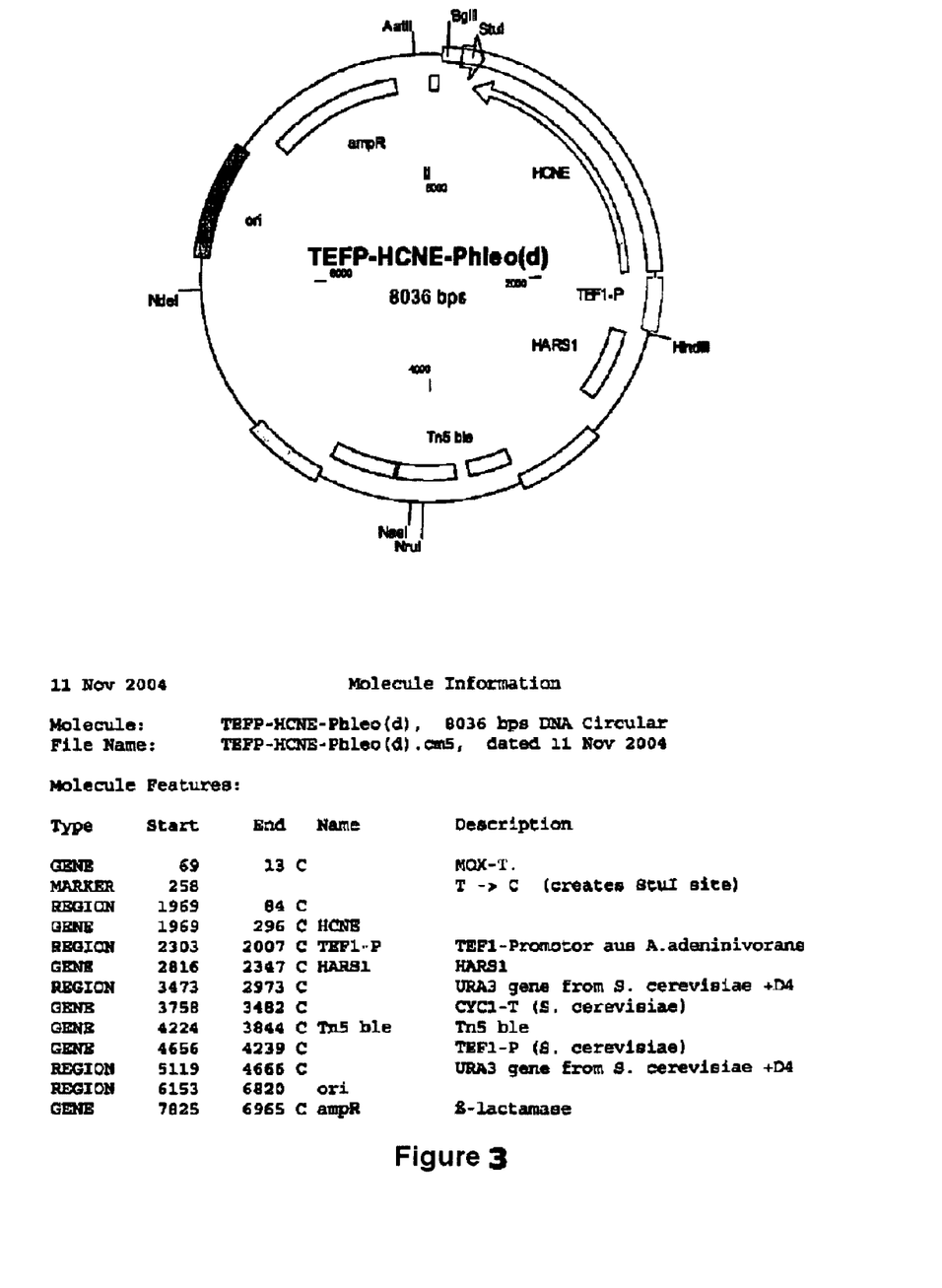
FIG. 3 shows a plasmid type of a calnexin expression plasmid, TEFP-HCNE-Phleo, used in a recombinant yeast host cell.

In experiments, two expression plasmids were used that contained the calnexin gene of *Hansenula polymorpha*. In an expression plasmid with the name HCNE-Phleo ('HCNE' derives from: *Hansenula* calnexin; 'Phleo' derives from genes resistant against the antibiotic selection phleomycin), the calnexin gene was flanked by its original transcription promoter and its original terminator. This plasmid is illustrated in FIG. 2. In the expression plasmid illustrated in FIG. 3, TEFP-HCNE-Phleo ('TEFP' derives from transcriptase elongation factor promoter), the calnexin gene was controlled by the TEF1 promoter from the yeast *Arxula adeninivorans* and the MOX terminator from *Hansenula polymorpha*. The TEF promoter used in this vector to control CNE expression can be inserted as a universal element for expression in various yeast types (see Klabunde, J, Kunze, G, Gellissen, G, and Hollenberg, C P, 'Integration of heterologous genes in several yeast species using vectors containing a *Hansenula polymorpha*-derived DNA-targeting element.' *FEMS Yeast Research* 4, 185-198, 2003). Both expression plasmids were subsequently used for supertransformation of three different recombinant strains of *Hansenula polymorpha*, which in each case secreted a heterologous protein. Of the three tested recombinant proteins, it was known that these were modified by a posttranslational glycosylisation in the host cells of the *Hansenula polymorpha*. The following recombinant strains of *Hansenula polymorpha* were chosen for the supertransformation:

a) RB11/AlgElsyn 52-4, which secretes a bacterial alginate C5 epimirase, b) RB11/Conphys 3-68, which secretes a synthetic 'consensus' phytase, c) RB11/FMD-MFIFND 23-2, which secretes a variant human γ-interferon, which is over-glycosylated when *Hansenula polymorpha* is used a large extent, and d) RB11/HSA 56-1, which secretes a human serum albumin.

Figure 4:
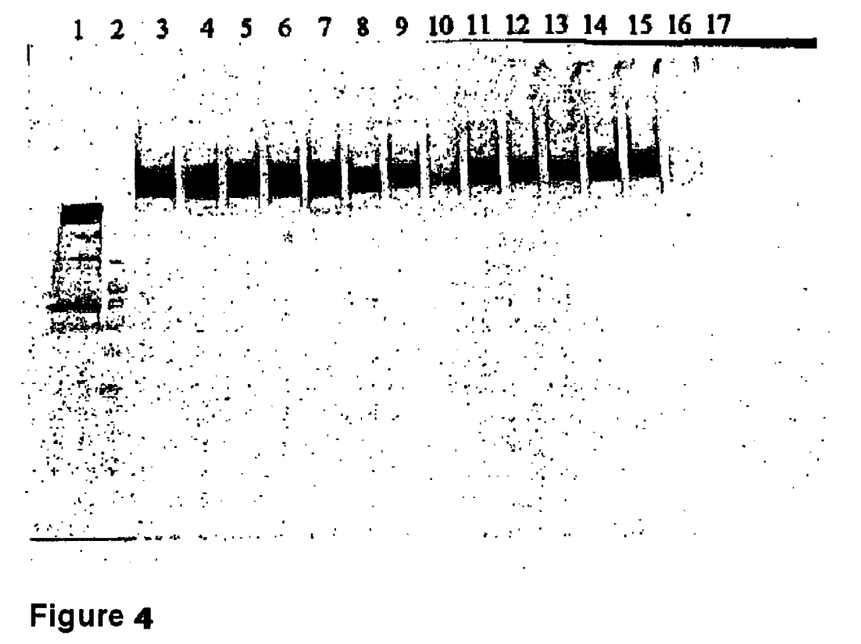
FIG. 4 shows a Western blot of a culture supernatant of a strain of yeast cells that, according to the invention, cause the secretion of alginate C5 epimerase.

Each of these strains was supertransformed with one of the two previously mentioned expression plasmids (HCNE-Phleo or TEFP-HCNE-Phleo). The supertransformants were selected with respect to resistance against the antibiotic phleomycin. After stabilisation, the supertransformants were cultivated using the conditions for heterologous protein expression, and the secreted heterologous proteins were analysed using Western blots or the SDS-PAGE/Coomassie stain. FIG. 4 shows an example Western blot of the culture supernatant from a recombinant *Hansenula polymorpha* strain RB11/AlgElsyn 52-4, which expresses the bacterial alginate C5 epimerase and was supertransformed with the expression plasmid HCNE-Phleo (d) (track 3-8) or TEFP-HCNE (tracks 9-15). Track 1 shows an AlgEl Standard (*E coli*), and track 2 shows a protein-size marker. Track 16 shows for comparison a non-supertransformed recombinant strain of RB11/AlgElsyn 52-4, and track 17 shows a control strain, which is not recombinant. The results of this analysis, in particular FIG. 4, clearly show an increased quantity of secreted proteins using the analysed supertranformants. This is true for both of the calnexin expression plasmids used.

The number of copies of the expression vectors in the three tested recombinant strains was unchanged, so the increase in the quantity of protein is not attributed to a gene dosage effect, but instead solely to the effect of the calnexin. The positive effect of the calnexin overexpression was detectable using strains with a reduced number of integrated foreign gene vectors (2 copies per cell; RB11/AlgElsyn 52-4), as well as using strains with a larger number of integrated foreign gene vectors (appx 50 copies per cell; RB11/FMD-MFIFNG 23-2 and RB11/Conphys 3-68). The positive effect of the calnexin overexpression was also detectable over the total range of the foreign protein production (a few milligrams of IFN gamma per liter in RB11/FMD-MFIFNG 23-2; 1-2 grams of epimerase per liter in RB11/AlgElsyn 52-4; 13.5 grams of phytase per liter in RB11/Conphys 3-68) in yeast. Additionally, for a more exact detection of the effect of the calnexin overexpression on the heterologous protein secretion, the HSA production in strain 56-1 and in selected calnexin supertransformants was quantified and compared using ELISA (see appendix 1). Furthermore, the strain RB11/HSA 56-1 was supertransformed with a vector without a calnexin gene, in order to provide evidence that the increase in production is attributed solely to the additional copies of calnexin and not to another vector sequences.

For this, four control strain vectors (mock HSA #1 to #4), which arose from the transformation of HSA 56-1 with the empty vector pPhleo(d), were tested in same way for their HSA expression capability.

In all, the following strains were tested:

HSA56-1 (background strain)

C10-7 and C10-9 (Calnexin supertransformants)

Mock (RB11, supertransformed with pFPMT)

Mock HSA (56-1, supertransformed with a vector without copies of calnexin)

The following HSA quantities were determined using ELISA:

| Strain | 56-1 | C10-7 | C10-8 | Mock | Mock HSA Nr. | | | | Average |
| --- | --- | --- | --- | --- | --- | --- | --- | --- | --- |
|  |  |  |  |  | #1 | #2 | #3 | #4 |  |
| HSA [mg/L] | 6.73 | 14.79 | 14.06 | 0 | 6.72 | 7.59 | 6.20 | 6.56 | 6.77 |
| Factor | 1 | 2.2 | 2.1 | 0 | 1 | 1.1 | 0.9 | 1.0 | 1.0 |

As in the other examples, the tested calnexin supertranformants showed a significant increase in the secretion of the heterologous protein. In contrast, the supertransformants that arose from the transformation of HSA 56-1 with the empty vector pPhleo (d) showed similar quantities of HSA in the remainder as those of the background strain HSA56-1.

The overexpression of calnexin as chaperone of the endoplasmatic reticulum using a recombinant strain of *Hansenula polymorpha*, which expresses and secretes a glycosylated heterologous protein, therefore leads to a significant improvement of the secretion efficiency and the yield of these heterologous proteins.

Materials and Methods:

The methods and media used for the construction of the expression vector, as well as for the transformation, cultivation, and analysis of the yeast cells, and also for the base vectors and yeast strains are described in:

G Gellissen (ed), '*Hansenula polymorpha*—biology and applications', Wiley-VCH, Weinheim 2002, in particular, in the chapters:

A Degelmann, 'Methods' and

M Suckow, G Gellissen, 'The expression platform based on *Hansenula polymorpha* strain RB11 and its derivatives—history, status and perspectives.'

The invention claimed is:

1. A method for producing a protein, the method comprising the steps:

a) preparing host cells from at least one yeast type of genera *Saccharomyces*, *Schizosaccharomyces*, *Kluyveromyces*, *Hansenula*, *Pichia*, *Arxula*, *Schwanniomyces*, *Candida*, and *Yarrowia*, which along with their at least one, own, homologous DNA sequence coding for at least a first calnexin, also contain in each case, at least one recombinant DNA sequence coding for the protein, as well as at least one additional recombinant DNA sequence coding for a second calnexin, wherein the protein in the host cell represents a heterologous, secretable protein;

b) causing the host cells, with the help of at least one sequence coding for the protein, to express the heterologous protein, and, with at least one additional sequence coding for at least a second calnexin, to overexpress calnexins;

c) causing the host cells to secrete the heterologous protein, and d) separating the secreted heterologous protein.

2. The method according to claim 1, wherein in step a) host cells are prepared that contain several additional recombinant DNA sequences coding for a second calnexin.

3. The method according to claim 2, wherein the several additional recombinant DNA sequences are identical to one another.

4. The method according to claim 1, wherein the first and the second calnexins are at least structurally similar.

5. The method according to claim 4, wherein the additional recombinant DNA sequences coding for calnexin are at least similar to one of the homologous DNA sequences coding for calnexin.

6. The method according to claim 1, wherein all recombinant DNA sequences coding for the heterologous protein are identical.

7. The method according to claim 1, wherein the step of preparing host cells, at least one DNA sequence coding for the heterologous protein and at least one additional DNA sequence coding for a second calnexin are inserted into the host cell with the aid of vectors.

8. The method according to claim 7, wherein the vectors are integrated into the genome of the cell.

9. The method according to claim 7, wherein each DNA sequence coding for the heterologous protein and each DNA sequence coding for a second calnexin is inserted into a vector.

10. The method according to claim 7, wherein plasmids are used as vectors.

11. The method according claim 1, wherein the step of preparing the host cells includes:
   a1) preparing recombinant host cells that contain in each case at least one recombinant DNA sequence coding for a heterologous protein, and
   a2) subsequently, transforming the recombinant host cells by inserting into the recombinant host cells at least one additional DNA sequence coding in each case for at least a second calnexin, with the aid of vectors.

12. The method according to claim 1, wherein the step of preparing the host cells includes:
   a1) preparing recombinant host cells that contain in each case at least one additional recombinant DNA sequence coding for a second calnexin, and
   a2) subsequently, transforming the recombinant host cells by inserting into the recombinant host cells at least one recombinant DNA sequence coding in each case for the heterologous protein.

13. The method according to claim 1, wherein the step of preparing the host cell includes inserting at least one recombinant DNA sequence coding for the heterologous protein as well as at least one recombinant DNA sequence coding for at least a second calnexin into the host cell at the same time.

14. The method according to claim 11, wherein the method further includes, before step a), preparing expression plasmids as vectors that contain a DNA sequence for at least a second calnexin or a DNA sequence coding for the heterologous protein.

15. The method according to claim 14, wherein the expression plasmids are prepared by isolating and cloning a calnexin gene into a plasmid, wherein the calnexin gene is inserted between a homologous or heterologous promoter and a homologous or heterologous terminator.

16. The method according to claim 1, wherein in step a), host cells are prepared from a methylothrophenic yeast.

17. The method according to claim 1, wherein in step a), host cells are prepared from a recombinant yeast, which in each case contain at least one recombinant DNA sequence coding for a heterologous protein, wherein the heterologous protein is a protein that is post-translationally modified during at least one of step b) and step c).

18. The method according to claim 17, wherein the heterologous protein is a protein that is post-translationally glycosylated.

19. The method according to claim 18, wherein the heterologous protein is a protein from a group that includes γ-interferon, alginate epimerase, and consensus phytase and variants of γ-interferon, alginate epimerase, and consensus phytase.

20. The method according to claim 1, wherein the heterologous protein is a protein from a group that includes γ-interferon, α-interferon, hirudin, serum albumin, alginate epimerase, consensus phytase, and variants of γ-interferon, α-interferon, hirudin, serum albumin, alginate epimerase, and consensus phytase.

21. The method according to claim 16, wherein the methylothrophenic yeast is selected from the genera *Hansenula* and *Pichia*.

22. The method according to claim 21, wherein in step a), host cells are prepared from the yeast *Hansenula polymorpha*.

* * * * *

UNITED STATES PATENT AND TRADEMARK OFFICE
CERTIFICATE OF CORRECTION

PATENT NO.         : 7,858,343 B2
APPLICATION NO.    : 11/667935
DATED              : December 28, 2010
INVENTOR(S)        : Gerd Gellissen et al.

It is certified that error appears in the above-identified patent and that said Letters Patent is hereby corrected as shown below:

On the Title Page, Item (73) Assignee, should read as follows:

Item --(73) Assignee: Artes Biotechnology GmbH, Essen (DE) and
Rhein Biotech Gesellschaft Fur Neue Biotechnologische Prozesse Und Produkte MBH, Dusseldorf (DE)--.

Signed and Sealed this
Twenty-fifth Day of September, 2012

David J. Kappos
*Director of the United States Patent and Trademark Office*